(12) United States Patent
Cummings et al.

(10) Patent No.: US 9,024,002 B2
(45) Date of Patent: May 5, 2015

(54) **COMPOSITIONS AND METHODS FOR DETECTION OF *SALMONELLA* SPECIES**

(71) Applicant: Life Technologies Corporation, Carlsbad, CA (US)

(72) Inventors: Craig Cummings, Pacifica, CA (US); Olga Petrauskene, San Carlos, CA (US); Lily Wong, San Mateo, CA (US); Allison De Los Reyes, Belmont, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/788,715

(22) Filed: Mar. 7, 2013

(65) Prior Publication Data

US 2014/0080130 A1 Mar. 20, 2014

Related U.S. Application Data

(60) Provisional application No. 61/701,316, filed on Sep. 14, 2012.

(51) Int. Cl.
*C12Q 1/68* (2006.01)
*C12P 19/34* (2006.01)

(52) U.S. Cl.
CPC ............ *C12Q 1/689* (2013.01); *C12Q 2600/16* (2013.01)

(58) Field of Classification Search
CPC .............................. C12Q 1/689; C12Q 1/6888
See application file for complete search history.

(56) References Cited

PUBLICATIONS

Herrera-Leon et al. Multiplex PCR for distinguishing the most common phase-1 flagellar antigens of *Salmonella* spp. J. Clinical Microbiology (2004) vol. 42, No. 6, pp. 2581-2586.*
Herrera-Leon et al. *Salmonella enterica* subsp. enterica serovar Hadar FliC (fliC) gene, partial cds. GenBank Accession No. AY434693. (2004).*
Echeita et al. Multiplex PCR based detection and identification of the most common *Salmonella* second-phase flagellar antigens. Res. Microbiology (2002) vol. 153, pp. 107-113.*
Echeita et al. *Salmonella* Hadar partial fljB gene for internal variable region. GenBank Accession No. AJ292278. (2005).*
Abd-Elsalam, K.A. Bioinformatic tools and guideline for PCR primer design. African J. Biotech. (2003) vol. 2, No. 5, pp. 91-95.*
Wittwer et al. Real-time multiplex PCR assays. Methods (2001) vol. 25, pp. 430-442.*
Akiba et al., "Rapid identification of *Salmonella enterica* serovars, Typhimurium, Choleraesuis, Infantis, Hadar, Enteritidis, Dublin and Gallinarum, by multiplex for", Journal of Microbiological Methods, vol. 85, No. 1, Apr. 2011, 9-15.

Den Bakker, "A Whole-Genome Single Nucleotide Polymorphism-Based Approach to Trace and Identify Outbreaks Linked to a Common *Salmonella enterica* subsp. Enterica Serovar Montevideo Pulsed-Field Gel Electrophoresis Type," Applied Environmental Microbiology, vol. 77, No. 24, Dec. 2011, 8648-8655.
Genbank Accession No. NC_011083 , Jan. 27, 2012.
Hong et al., "A Rapid Screen of Broth Enrichments for *Salmonella enterica* Serovars Enteriditis, Hadar, Heidelberg, and Typhimurium by Using an Allelotyping Multiplex PCR That Targets O -and H-Antigen Alleles", Journal of Food Protection, vol. 72, No. 11, 2009, 2198-2201.
Hong et al., "Rapid screening of *Salmonella enterica* serovars Enteritidis, Hadar, Heidelberg and Typhimurium using a serologically-corrective allelotyping PCR targeting the O and H antigen alleles", BMC Microbiology, vol. 8, No. 178, Jan. 1, 2008, 1-8.
Kim et al., "Use of Fourier transform infrared spectra of crude bacterial lipopolysaccharides and chemometrics for differentiation of *Salmonella enterica* serotypes", Journal of Applied Micribiology, vol. 99, No. 2, 2005, 411-417.
Liu, "Novel Virulence Gene and Clustered Regularly Interspaced Short Palindromic Repeat (Crispr) Multilocus Sequence Typing Scheme for Subtyping of the Major Serovars of *Salmonella enterica* subsp. enterica", Applied and Environmental Microbiology, vol. 77, No. 6, Mar. 2011, 1946-1956.
McCarthy et al., "Sensitive and rapid molecular detection assays for *Salmonella enterica* serovars Typhimurium and Heidelberg", Journal of Food Protection, vol. 72, No. 11, Nov. 2009, 2350-2357.
O'Regan et al., "Development of a real-time multiplex PCR assay for the detection of multiple *Salmonella* serotypes in chicken samples," BMC Microbiology, vol. 8, No. 156, Sep. 21, 2008, 1-11.
Sukhnanand et al., "DNA sequence-based subtyping and evolutionary analysis of selected *Salmonella enterica* serotypes", Journal of Clinical Microbiology, vol. 43, No. 8, Aug. 2005, 3688-3698.
Unknown, "National Enteric Disease Surveillance: *Salmonella* Surveillance Overview," Enteric Diseases Epidemiology Branch, National Center for Emerging and Zoonotic Infectious Diseases, CDC, Jul. 2011, 1-12.
Wise et al., "Predicting *Salmonella enterica* serotypes by repetitive sequence-based PCR", Journal of Microbiological Methods, vol. 76, No. 1, Jan. 2009, 18-24.
Xi et al., "An Enhanced Discriminatory Pulsed-Field Gel Electrophoresis Scheme for Subtyping *Salmonella* Serotypes Heidelberg, Kentucky, SaintPaul, and Hadar", Journal of Food Protection, vol. 71, No. 10, 2008, 2067-2072.
Zhou et al., "Identification of Genes to Differentiate Closely Related *Salmonella* Lineages, " PLoS One, vol. 8, No. 2, Feb. 2013, e55988 (1-8).

* cited by examiner

*Primary Examiner* — Teresa E Strzelecka
*Assistant Examiner* — David Thomas

(57) ABSTRACT

Described are compositions, methods and kits for detection and/or differential detection of serovars of *Salmonella enterica* subsp. *enterica* serovar such as S. Heidelberg and S. Hadar in samples. Some embodiments relate to multiplex amplification based molecular assays.

11 Claims, No Drawings

COMPOSITIONS AND METHODS FOR DETECTION OF *SALMONELLA* SPECIES

CROSS-REFERENCE(S) TO RELATED APPLICATION

This application claims priority under 35 U.S.C. §119(e) of U.S. Provisional Application No. 61/701,316, filed Sep. 14, 2012, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on May 22, 2013, is named LT00719_SL.txt and is 3,048 bytes in size.

FIELD

The present disclosure, in some embodiments, relates to compositions, methods and kits for detection of a *Salmonella enterica* subsp. *enterica* serovar microorganism contaminant in a sample. Some embodiments describe compositions, methods and kits for differentially detecting a *Salmonella enterica* subsp. *enterica* serovar Heidelberg (S. Heidelberg) microorganism. Some embodiments describe compositions, methods and kits for differentially detecting a *Salmonella enterica* subsp. *enterica* serovar Hadar (S. Hadar) microorganism.

BACKGROUND

Identification of bacterial contamination in food often occurs subsequent to an outbreak of a foodborne illness. Bacteria of *Salmonella enterica* subsp. *enterica* serovars are frequently identified as a food contaminant of many foodborne illnesses.

Ingestion of S. Heidelberg and S. Hadar can result in Salmonellosis. Salmonellosis is characterized by diarrhea, fever, and abdominal cramps that typically arise 12 to 72 hours after infection. Salmonellosis usually lasts 4 to 7 days, and most people recover without treatment. In some cases *Salmonella* infection can enter the bloodstream leading to sepsis and can ultimately cause death if not treated. Children under the age of 5 years are most likely to get Salmonellosis. Children, the elderly, and immunocompromised are most likely to have severe infections.

S. Hadar infections have been linked to catfish, sliced deli meats, turkey burgers, and handling of live poultry (e.g., chicks, ducklings, turkeys)

S. Heidelberg infections have been linked to eggs, chicken, pork, salmon, and cheddar cheese. Recently, S. Heidelberg has been linked to outbreaks in ground turkey, and Kosher broiled chicken livers. A routine inspection by the FDA recently (May, 2012) detected S. Heidelberg at a large Iowa poultry house used for egg production. S. Heidelberg in egg layers are a concern since S. Heidelberg can infect eggs via the transovarian route in a manner similar to *Salmonella Enteritidis*, and S. Heidelberg has caused several egg associated outbreaks resulting in human illness and death. Eating eggs outside the home was identified as a primary risk factor for illness due to S. Heidelberg infection.

S. Heidelberg is one of the five serotypes most frequently isolated in human cases of salmonellosis in the U.S. The rise in prevalence of this serovar has been accompanied by increasing antimicrobial resistance. S. Heidelberg appears to be a highly clonal serovar, with 34 of 36 global isolates in the *Salmonella enterica* MLST database having an identical sequence type (ST15), and the other two (one from the US, and one from Australia) differing from this canonical serotype at only a single locus. A S. Heidelberg organism, if consumed in contaminated food, causes salmonellosis which is often characterized by fever, vomiting, diarrhea, abdominal cramps, and severe dehydration.

A PCR and gel-based molecular serotyping method for the detection and identification of S. Hadar, S. Heidelberg, *S. Enteritidis*, and *S. Typhimurium* was designed based on detecting the combination of O-antigen, phase 1 flagellar antigen (H1) and phase 2 flagellar antigen genes (H2). The O: H1: H2 assignment for S. Hadar and S. Heidelberg is C2: z10: e,n,x and B: r: 1,2, respectively. However, because other *Salmonella enterica* serotypes also carry each of these genes, this method is not sufficient to differentially identify a single serotype due to cross-reactivity. In some cases a single base pair difference in the flagellin gene sequence results in an amino acid change that displays an epitope with a different serotype. The developers of this test report that the H2 allelotyping primers cannot distinguish serovars Heidelberg (B: r: 1,2) from Bradford (B: r: 1,5), Winneba (B: r: 1,6), or Remo (B: r: 1,7), and cannot distinguish serovar Hadar (C2: z10: e,n,x) from Glostrup (C2: z10: e,n,z15).

Some S. Heidelberg-specific assays described in the literature are molecular serotyping assays based on a set of four multiplex PCR reactions targeting five O-antigen loci, the fliC gene, and the fljB gene. Although very specific, the complexity of this assay makes it unsuitable for specific detection of S. Heidelberg. Another multiplex test known is an assay that detects both S. Heidelberg and *S. Typhimurium* performed in combination with another assay that only detects *S. Typhimurium*. A positive signal from the first, but not the second assay indicates the presence of S. Heidelberg. Two step assays are always time consuming and can lead to errors.

Assays for rapid, sensitive, and specific detection of *Salmonella enterica* pathogens are extremely important from both a public health and economic perspective. There exists a need for novel assays and methods for detecting and differentiating various serovars of *Salmonella enterica* subsp. *enterica* such as S. Hadar and S. Heidelberg from other *Salmonella enterica* serovars to test food and other contaminated samples. Some potential uses would be identification of a pathogen in a contaminated food to identify a contaminant; and identification of a pathogen in a clinical sample to make a differential diagnosis of what microbe is causing a particular disease.

SUMMARY

The present disclosure, in some embodiments, describes compositions, kits and methods of use thereof for detection of one or more microorganisms and/or strains and/or serotypes of a *Salmonella enterica* subsp. *enterica*. These *Salmonella enterica* subsp. *enterica* microbes are present as contaminants in a sample. Samples that can be tested by methods of the disclosure to detect a microbial contaminant therein include but are not limited to a food sample (processed food samples and raw food samples), a beverage sample, an agricultural sample, a produce sample, an animal sample, a clinical sample, an environmental sample, a biological sample, a water sample and an air sample.

Some embodiments relate to compositions comprising isolated nucleic acid sequences that are operable or able to specifically hybridize to nucleic acid regions that are uniquely found in a *Salmonella enterica* subsp. *enterica* microbes under conditions of hybridization. Nucleic acid regions uniquely found in a *Salmonella enterica* subsp. *enterica* serovar (including complementary regions thereof, fragments thereof, variants, alleles and sequences having 90% identity thereto) are referred to herein as "serovar specific target nucleic acids" or as "*Salmonella enterica* subsp. *enterica* serovar specific target nucleic acids". In some embodiments a serovar specific target nucleic acid is a S. Hadar specific target nucleic acid or a S. Heidelberg specific target nucleic acid sequence.

In some embodiments, a *Salmonella enterica* subsp. *enterica* serovar specific target nucleic acid is a fljB gene encoding the phase two flagellin, or an allele (e.g., $fljB_{e,n,x}$), variant and/or fragment thereof; a fliC gene encoding the phase one flagellin, or an allele (e.g. $fliC_{z10}$), variant and/or fragment thereof; an arsR gene encoding a transcriptional repressor (SeHA_C3265); a phage integrase gene (SeHA_C3266); a helicase-encoding gene (SeHA_C4894, SeHA_C4896, and SeHA_C4897); a type II restriction methylase encoding gene (SeHA_C4895); or SeHA_C4893, which encodes a hypothetical protein.

Some embodiments of the present disclosure describe compositions comprising isolated oligonucoleotide sequences. In some embodiments oligonucleotide compositions of the disclosure are primer and/or probe nucleic acid sequences that are specific to hybridize to a *Salmonella enterica* subsp. *enterica* serovar specific target nucleic acid.

One embodiment describes compositions comprising isolated nucleic acid sequences having the nucleotide sequence of SEQ ID NOS: 1-12, fragments thereof, complements thereof, sequences having about 90% identity to the foregoing sequences and labeled derivatives thereof.

Some embodiments describe compositions comprising a set of oligonucleotide primers for simultaneous use in a multiplex amplification (e.g., PCR) process for the detection of a *Salmonella enterica* subsp. *enterica* serovar and comprise at least two primer sets, each primer set having at least a forward primer and at least a reverse primer, all primers operable to hybridize to a serovar specific target nucleic acids.

In one embodiment, a set of oligonucleotide primers for simultaneous use in a multiplex PCR process comprise primers operable to hybridize to and amplify (under appropriate amplification conditions) a S. Heidelberg serovar specific target nucleic acid. Some exemplary non-limiting sets of S. Heidelberg specific primers comprise at least two primer sets selected from a first primer set having SEQ ID NO: 1 and SEQ ID NO: 2; a second primer set having SEQ ID NO: 4 and SEQ ID NO: 5; or sequences comprising at least 90% nucleic acid sequence identity thereof, or a labeled derivative thereof.

In one embodiment, a set of oligonucleotide primers for simultaneous use in a multiplex PCR process comprise primers operable to hybridize to and amplify (under appropriate amplification conditions) a S. Hadar specific target nucleic acid. Some exemplary non-limiting set of S. Hadar specific primers comprise at least two primer sets selected from a first primer set having SEQ ID NO: 7 and SEQ ID NO: 8; a second primer set having SEQ ID NO: 10 and SEQ ID NO: 11; or sequences comprising at least 90% nucleic acid sequence identity thereof, or a labeled derivative thereof.

Fragments of nucleic acid sequences described herein include without limitation nucleic acids having at least 10, at least 15, or at least 20 contiguous nucleic acids of a nucleic acid sequence as described herein. Nucleic acid sequences of the disclosure, in some embodiments, are primers and/or probes. In some embodiments, primers of the disclosure may be degenerate primers. Primers and probes may be labeled. In some embodiments, isolated nucleic acid sequence compositions of the disclosure may comprise one or more label, such as, but not limited to, a dye, a radioactive isotope, a chemiluminescent label, a fluorescent moiety, a bioluminescent label, an enzyme, and combinations thereof. In some embodiments primers and probes can comprise chemical and/or biological derivatives of the sequences described here.

Some embodiments of the present disclosure describe methods for detection of *Salmonella enterica* subsp. *enterica* serovar microorganisms in a sample and comprise detection of the presence of one or more serovar specific target nucleic acid sequences. Some methods disclosed here are singleplex methods and can detect the presence of one serovar specific target region from nucleic acids present in a sample. Some methods disclosed herein are multiplex methods which can simultaneously detect the presence of one or more targets of a serovar; and/or simultaneously detect one or more targets of one or more serovars; and/or simultaneously detect the presence of one or more internal positive controls (IPC) along with one or more serovar specific target nucleic acid sequences, from nucleic acids present in a sample.

Some embodiments describe methods for detecting a *Salmonella enterica* subsp. *enterica* serovar microorganism in a sample comprising: hybridizing at least a first pair of nucleic acid amplification primers specific to hybridize to a first serovar specific target nucleic acid, a fragment thereof, a complements thereof, an allele thereof, and/or a variant thereof, wherein the first serovar specific target nucleic acid is present in a polynucleotide sequence present in the sample; amplifying at least the first serovar specific target nucleic acid or a fragment, a complement, an allele and/or a variant thereof to obtain at least a first amplified serovar specific product; and detecting the first amplified serovar specific product; wherein detection of the first amplified serovar specific product is indicative of the presence of one *Salmonella enterica* subsp. *enterica* serovar microorganism in the sample. Absence of an amplified product is indicative of the absence of that *Salmonella enterica* subsp. *enterica* serovar microorganism in the sample. In some embodiments, at least two pairs of nucleic acid amplification primers can be used, wherein the second pair of nucleic acid amplification primers are specific to hybridize to a second serovar specific target nucleic acid sequence and produce a second amplified serovar specific products, wherein detection of the first and/or the second amplified products is indicative of the presence of a *Salmonella enterica* subsp. *enterica* in the sample.

Exemplary serovars detected are S. Heidelberg and S. Hadar, wherein the detection of one or more S. Heidelberg specific target nucleic acids is indicative of the presence of a S. Heidelberg microorganism and wherein the detection of one or more S. Hadar specific target nucleic acids is indicative of the presence of a S. Hadar microorganism in a sample.

One example embodiment method for detection of an S. Heidelberg in a sample comprises: hybridizing at least a first pair of nucleic acid amplification primers comprising nucleic acids of SEQ ID NO: 1 and SEQ ID NO: 2 and/or primers having SEQ ID NO: 4 and SEQ ID NO: 5, and/or complements thereof, and/or sequences having at least 90% homology thereto, to at least a first target polynucleotide sequence present in the sample; amplifying at least the first target polynucleotide sequence or a fragment or a complement thereof to obtain at least one amplified target polynucleotide sequence; and detecting the at least one amplified target polynucleotide sequence; wherein detection of the at least one amplified target polynucleotide sequence is indicative of the presence of a S. Heidelberg organism in the sample. In some embodiments, at least two primer sets selected from a primer set having SEQ ID NO: 1 and SEQ ID NO: 2 and/or a primer set having SEQ ID NO: 4 and SEQ ID NO: 5, and/or a primer set having complements of the foregoing sequences, and/or a primer set having sequences having at least 90% homology to the foregoing primer sets can be hybridized to sample nucleic acids and subject to multiplex amplification conditions to obtain one or more amplification products. Detection of one or both amplification products is indicative of the presence of a S. Heidelberg serovar organism in the sample. In some embodiments, detection of both the first and the second amplified products confirms the presence of S. Heidelberg.

A method to detect a S. Heidelberg can further comprise using a probe to detect the amplified target polynucleotide sequence wherein a probe can comprises a sequence of SEQ ID NO: 3, SEQ ID NO: 6, fragments having at least 10 contiguous nucleotides thereof, complements thereof, and sequences having at least 90% homology thereto. Hybridization of a probe can be used to identify a serovar.

One embodiments method for detection of an S. Hadar in a sample comprises: hybridizing at least a first pair of nucleic acid amplification primers comprising nucleic acids of SEQ ID NO: 7 and SEQ ID NO: 8 and/or primers having SEQ ID NO: 10 and SEQ ID NO: 11, and/or complements thereof, and/or sequences having at least 90% homology thereto, to at least a first target polynucleotide sequence present in the sample; amplifying at least the first target polynucleotide sequence or a fragment or a complement thereof to obtain at least one amplified target polynucleotide sequence; and detecting the at least one amplified target polynucleotide sequence; wherein detection of the at least one amplified target polynucleotide sequence is indicative of the presence of a S. Hadar organism in the sample. In some embodiments, at least two primer sets selected from a primer set having SEQ ID NO: 7 and SEQ ID NO: 8 and/or a primer set having SEQ ID NO: 10 and SEQ ID NO: 11, and/or a primer set having complements of the foregoing sequences, and/or a primer set having sequences having at least 90% homology to the foregoing primer sets can be hybridized to sample nucleic acids and subject to multiplex amplification conditions to obtain one or more amplification products. Detection of one or both amplification products is indicative of the presence of a S. Hadar serovar organism in the sample. In some embodiments, detection of both the first and the second amplified products confirms the presence of S. Hadar.

In some embodiments, an amplification can be preceded or simultaneously coupled with hybridization of a labeled probe, such as a TaqMan® probe, to a target nucleic acid prior to the commencement of the polymerase reaction.

A method to detect a S. Hadar can further comprise using a probe to detect the amplified target polynucleotide sequence. In some embodiments, a probe can comprises a sequence of SEQ ID NO: 9, SEQ ID NO: 12, fragments having at least 10 contiguous nucleotides thereof, complements thereof, and sequences having at least 90% homology thereto. Probes can be used to in additional method steps comprising identification of a serovar.

In some embodiments, not detecting any amplified product using methods described above can be used to exclude the presence of a microorganism of a particular serovar in a sample. In some embodiments, detecting and/or identifying an amplified nucleic acid comprises one or more methods such as but not limited to hybridization, mass spectrometry, nanostring, microfluidics, chemiluminescence, enzyme technologies and combinations thereof. Some embodiments comprise identifying the particular microbial serovar and can comprise methods such as DNA sequencing. In some embodiment methods described here, nucleic acids (RNA/DNA) can be extracted from a sample suspected to contain a microorganism to be detected prior to amplification or detection. A method can further comprise one or more steps such as: enrichment of microorganisms in a sample prior to nucleic acid extraction; and/or nucleic acid extraction from microorganisms in a sample; and/or nucleic acid isolation from a sample; and/or nucleic acid purification from a sample; and/or lysing bacterial cells from a sample prior to hybridization/amplification with primers and/or probes.

Methods of the present disclosure can be used to detect the presence of a *Salmonella enterica* subsp. *enterica* in a sample such as but not limited to a food sample, a beverage sample, an agricultural sample, a produce sample, an animal sample, a human sample, a clinical sample, an environmental sample, a biological sample, a water sample and/or an air sample.

In some embodiments, methods of the disclosure can be performed on an automated system. Automation decreases the time as well as efficiency and allows processing multiples samples. Automated systems may comprise platforms to automate sample preparation such as but not limited to Mag-MAX™ Express-96 Magnetic Particle Processor by Life Technologies Corporation; Pathatrix system by Life Technologies; MagNA Pure System by Roche; the QIAsymphony system by Qiagen, among others.

Detection in the methods above may be performed by a variety of methods, such as but not limited to, by a nucleic acid amplification reaction, the amplification reaction is an end-point determination, the amplification reaction is quantitative, the quantification is a real-time PCR, the real-time PCR is a SYBR® Green Assay or the real-time PCR is a TaqMan® Assay. Detection may in some embodiments be performed by hybridization using probes specific to amplified nucleic acid sequences encoding a target sequence. Combinations of amplification and hybridization may be used for detection according to some embodiments.

In some embodiments, hybridization may comprise at least a first probe and a second probe, the first probe further comprising a first label and said second probe further comprising a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye.

Some embodiments describe kits suitable for identifying the presence of a *Salmonella enterica* subsp. *enterica* serovar organism. A kit of the disclosure can comprise one or more sets of primers operable to hybridize to and amplify a serovar-specific target nucleic acid. An example kit may comprise at least one pair (or more than one) of forward and reverse PCR primer sets selected from a first primer set having SEQ ID NO: 1 and SEQ ID NO 2; a second primer set having SEQ ID NO: 4 and SEQ ID NO 5; a third primer set having SEQ ID NO: 7 and SEQ ID NO: 8; and/or a fourth primer set having SEQ ID NO: 10 and SEQ ID NO 11, and/or primer sets with sequences comprising at least 90% nucleic acid sequence identity to the primer sets described here and/or primer sets with complementary sequences to the primer sets described here and/or a labeled derivative of any of the foregoing primer sets; optionally at least one probe (or more than one) selected from probes selected from SEQ ID NO: 3; SEQ ID NO: 6; SEQ ID NO: 9; and/or SEQ ID NO:12; and/or sequences comprising at least 90% nucleic acid sequence identity thereto; and/or sequences having complementary sequences thereto; and/or a labeled derivative of any of the foregoing sequences; and one or more components selected from a group consisting of: at least one enzyme, dNTPs, at least one buffer, at least one salt, at least one control nucleic acid sample and an instruction protocol. Different primers and probes in a kit can be labeled with different labels to allow for detection of different amplified products and/or hybridized products.

In the following detailed description, certain aspects and embodiments will become evident. It should be understood that a given embodiment need not have all aspects and features described herein. It should be understood that these aspects and embodiments are merely exemplary and explanatory and are not restrictive of the present disclosure. It is to be understood that both the foregoing general description and the following detailed description are exemplary and explanatory only and are not restrictive of the present disclosure, as claimed.

DETAILED DESCRIPTION

For the purposes of interpreting of this specification, the following definitions may apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of:"

As used herein, the phrase "nucleic acid," "nucleic acid sequence," "oligonucleotide", and "polynucleotides" are interchangeable and not intended to be limiting.

As used herein, the phrase "hybridization conditions" or "stringent hybridization conditions" refers to hybridization conditions which can take place under a number of pH, salt and temperature conditions. The pH can vary from 6 to 9, preferably 6.8 to 8.5. The salt concentration can vary from 0.15 M sodium to 0.9 M sodium, and other cations can be used as long as the ionic strength is equivalent to that specified for sodium. The temperature of the hybridization reaction can vary from 30° C. to 80° C., preferably from 45° C. to 70° C. Additionally, other compounds can be added to a hybridization reaction to promote specific hybridization at lower temperatures, such as at or approaching room temperature. Among the compounds contemplated for lowering the temperature requirements is formamide. Thus, a polynucleotide is typically "substantially complementary" to a second polynucleotide if hybridization occurs between the polynucleotide and the second polynucleotide. As used herein, "hybridization" or "specific hybridization" refers to hybridization between two polynucleotides under stringent hybridization conditions.

As used herein, the term "polynucleotide" refers to a polymeric form of nucleotides of any length, either ribonucleotides, deoxynucleotides, or peptide nucleic acids (PNA), and includes both double- and single-stranded RNA, DNA, and PNA. A polynucleotide may include nucleotide sequences having different functions, including, for instance, coding regions, and non-coding regions such as regulatory regions. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. An "oligonucleotide" refers to a polynucleotide of the present disclosure, typically a primer and/or a probe.

As used herein a "target-specific polynucleotide" refers to a polynucleotide having a target-binding segment that is perfectly or substantially complementary to a target sequence, such that the polynucleotide binds specifically to an intended target without significant binding to non-target sequences under sufficiently stringent hybridization conditions. A target-specific polynucleotide can be e.g., a primer or probe and the subject of hybridization with its complementary target sequence.

The term "target sequence", "target specific nucleic acid" "target signature sequence" "target nucleic acid", "target" or "target polynucleotide sequence" refers to a nucleic acid of interest. Example targets of interest in some embodiments of this application include regions that are unique or specific to one or more *Salmonella enterica* subsp. *enterica* serovar encoding nucleic acids and fragments, complements and sequences with 90% homology thereto and include for example nucleic acid sequences that are unique to serovars S. Heidelberg and S. Hadar. The target sequence can be a polynucleotide sequence that is the subject of hybridization with a complementary polynucleotide, e.g. a primer or probe. The target sequence can be composed of DNA, RNA, an analog thereof, and including combinations thereof. The target sequence may be known or not known, in terms of its actual sequence and its amplification can be desired. The target sequence may or may not be of biological significance. Typically, though not always, it is the significance of the target sequence which is being studied in a particular experiment. As non-limiting examples, target sequences may include regions of genomic DNA, regions of genomic DNA which are believed to contain one or more polymorphic sites, DNA encoding or believed to encode genes or portions of genes of known or unknown function, DNA encoding or believed to encode proteins or portions of proteins of known or unknown function, DNA encoding or believed to encode regulatory regions such as promoter sequences, splicing signals, polyadenylation signals, etc.

As used herein an "amplified target polynucleotide sequence product" or "amplified product" refers to the resulting amplicon from an amplification reaction such as a polymerase chain reaction. The resulting amplicon product arises from hybridization of complementary primers to a target polynucleotide sequence under suitable hybridization conditions and the repeating in a cyclic manner the polymerase chain reaction as catalyzed by DNA polymerase for DNA amplification or RNA polymerase for RNA amplification.

As used herein, the "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art.

As used herein, "amplifying" and "amplification" refers to a broad range of techniques for increasing polynucleotide sequences, either linearly or exponentially. Exemplary amplification techniques include, but are not limited to, PCR or any other method employing a primer extension step. Other non-limiting examples of amplification include, but are not limited to, ligase detection reaction (LDR) and ligase chain reaction (LCR). Amplification methods may comprise thermal-cycling or may be performed isothermally. In various embodiments, the term "amplification product" or "amplified product" includes products from any number of cycles of amplification reactions.

In certain embodiments, amplification methods comprise at least one cycle of amplification, for example, but not limited to, the sequential procedures of: hybridizing primers to primer-specific portions of target sequence or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated.

Descriptions of certain amplification techniques can be found, among other places, in H. Ehrlich et al., Science, 252:1643-50 (1991), M. Innis et al., PCR Protocols: A Guide to Methods and Applications, Academic Press, New York, N.Y. (1990), R. Favis et al., Nature Biotechnology 18:561-64 (2000), and H. F. Rabenau et al., Infection 28:97-102 (2000); Sambrook and Russell, Molecular Cloning, Third Edition, Cold Spring Harbor Press (2000) (hereinafter "Sambrook and Russell"), Ausubel et al., Current Protocols in Molecular Biology (1993) including supplements through September 2005, John Wiley & Sons (hereinafter "Ausubel et al.").

The term "label" refers to any moiety which can be attached to a molecule and: (i) provides a detectable signal; (ii) interacts with a second label to modify the detectable signal provided by the second label, e.g. FRET; (iii) stabilizes hybridization, i.e. duplex formation; or (iv) provides a capture moiety, i.e. affinity, antibody/antigen, ionic complexation. Labeling can be accomplished using any one of a large number of known techniques employing known labels, linkages, linking groups, reagents, reaction conditions, and analysis and purification methods. Labels include light-emitting compounds which generate a detectable signal by fluorescence, chemiluminescence, or bioluminescence (Kricka, L. in Nonisotopic DNA Probe Techniques (1992), Academic Press, San Diego, pp. 3-28). Another class of labels are hybridization-stabilizing moieties which serve to enhance, stabilize, or influence hybridization of duplexes, e.g. intercalators, minor-groove binders, and cross-linking functional groups (Blackburn, G. and Gait, M. Eds. "DNA and RNA structure" in Nucleic Acids in Chemistry and Biology, 2.sup.nd Edition, (1996) Oxford University Press, pp. 15-81). Yet another class of labels effect the separation or immobilization of a molecule by specific or non-specific capture, for example biotin, digoxigenin, and other haptens (Andrus, A. "Chemical methods for 5' non-isotopic labelling of PCR probes and primers" (1995) in PCR 2: A Practical Approach, Oxford University Press, Oxford, pp. 39-54).

The terms "annealing" and "hybridization" are used interchangeably and mean the base-pairing interaction of one nucleic acid with another nucleic acid that results in formation of a duplex or other higher-ordered structure. The primary interaction is base specific, i.e. A/T and G/C, by Watson/Crick and Hoogsteen-type hydrogen bonding.

The term "end-point analysis" refers to a method where data collection occurs only when a reaction is substantially complete.

The term "real-time analysis" refers to periodic monitoring during PCR. Certain systems such as the Applied Biosystems 7500 Real-Time PCR System (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

The term "quenching" refers to a decrease in fluorescence of a first moiety (reporter dye) caused by a second moiety (quencher) regardless of the mechanism.

A "primer," as used herein, is an oligonucleotide that is complementary to a portion of target polynucleotide and, after hybridization to the target polynucleotide, may serve as a starting-point for an amplification reaction and the synthesis of an amplification product. Primers include, but are not limited to, spanning primers. A "primer pair" refers to two primers that can be used together for an amplification reaction. A "PCR primer" refers to a primer in a set of at least two primers that are capable of exponentially amplifying a target nucleic acid sequence in the polymerase chain reaction.

The term "probe" comprises a polynucleotide that comprises a specific portion designed to hybridize in a sequence-specific manner with a complementary region of a specific nucleic acid sequence, e.g., a target nucleic acid sequence. In certain embodiments, the specific portion of the probe may be specific for a particular sequence, or alternatively, may be degenerate, e.g., specific for a set of sequences. In certain embodiments, the probe is labeled. The probe can be an oligonucleotide that is complementary to at least a portion of an amplification product formed using two primers.

The terms "complement" and "complementary" as used herein, refer to the ability of two single stranded polynucleotides (for instance, a primer and a target polynucleotide) to base pair with each other, where an adenine on one strand of a polynucleotide will base pair to a thymine or uracil on a strand of a second polynucleotide and a cytosine on one strand of a polynucleotide will base pair to a guanine on a strand of a second polynucleotide. Two polynucleotides are complementary to each other when a nucleotide sequence in one polynucleotide can base pair with a nucleotide sequence in a second polynucleotide. For instance, 5'-ATGC and 5'-GCAT are complementary.

A "label" refers to a moiety attached (covalently or non-covalently), or capable of being attached, to an oligonucleotide, which provides or is capable of providing information about the oligonucleotide (e.g., descriptive or identifying information about the oligonucleotide) or another polynucleotide with which the labeled oligonucleotide interacts (e.g., hybridizes). Labels can be used to provide a detectable (and optionally quantifiable) signal. Labels can also be used to attach an oligonucleotide to a surface.

A "fluorophore" is a moiety that can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength.

The term "quencher" as used herein refers to a moiety that absorbs energy emitted from a fluorophore, or otherwise interferes with the ability of the fluorescent dye to emit light. A quencher can re-emit the energy absorbed from a fluorophore in a signal characteristic for that quencher, and thus a quencher can also act as a fluorophore (a fluorescent quencher). This phenomenon is generally known as fluorescent resonance energy transfer (FRET). Alternatively, a quencher can dissipate the energy absorbed from a fluorophore as heat (a non-fluorescent quencher).

As used herein the term "sample" refers to a starting material suspected of harboring a particular microorganism or group of microorganisms. A "contaminated sample" refers to a sample harboring a pathogenic microbe thereby comprising nucleic acid material from the pathogenic microbe. Examples of samples include, but are not limited to, food samples (including but not limited to samples from food intended for human or animal consumption such as processed foods, raw food material, produce (e.g., fruit and vegetables), legumes, meats (from livestock animals and/or game animals), fish, sea food, nuts, beverages, drinks, fermentation broths, and/or a selectively enriched food matrix comprising any of the above listed foods), water samples, environmental samples (e.g., soil samples, dirt samples, garbage samples, sewage samples, industrial effluent samples, air samples, or water samples from a variety of water bodies such as lakes, rivers, ponds etc.,), air samples (from the environment or from a room or a building), forensic samples, agricultural samples, pharmaceutical samples, biopharmaceutical samples, samples from food processing and manufacturing surfaces, and/or biological samples.

Disclosed are compositions, assays, methods and kits for the specific detection of *Salmonella enterica* subsp. *enterica* serovar microorganisms from samples including clinical samples, food samples, complex food matrices, water, a beverage sample, a fermentation broth, a forensic sample, an environmental sample (e.g., soil, dirt, garbage, sewage, air, or water), including food processing and manufacturing surfaces, and/or biological samples.

A sample may be tested directly, or may be prepared or processed in some manner prior to testing. For example, a sample may be processed to enrich any contaminating microbe and may be further processed to separate and/or lyse microbial cells contained therein. Lysed microbial cells from a sample may be additionally processed or prepares to separate, isolate and/or extract genetic material from the microbe for analysis to detect and/or identify the contaminating microbe. In some embodiments described here, as sample may be subject to separation to initially separate microbes of interest from other microbes and other sample components. For example, for complex food samples with complex components separation methods can be used to separate microorganisms from food. Separated microbes from samples can also be enriched prior to analysis. Analysis of a sample may include one or more molecular methods. For example, according to some exemplary embodiments of the present disclosure, a sample may be subject to nucleic acid amplification (for example by PCR) using appropriate oligonucleotide primers that are specific to one or more microbe nucleic acid sequences that the sample is suspected of being contaminated with. Amplification products may then be further subject to testing with specific probes (or reporter probes) to allow detection of microbial nucleic acid sequences that have been amplified from the sample. In some embodiments, if a microbial nucleic acid sequence is amplified from a sample, further analysis may be performed on the amplification product to further identify, quantify and analyze the detected microbe (determine parameters such as but not limited to the microbial strain, pathogenecity, quantity etc.).

As used herein "preparing" or "preparing a sample" or "processing" or processing a sample" refers to one or more of the following steps to achieve separation of microbes from sample components and in some embodiments optionally extraction and/or separation of a nucleic acid from a sample: (1) optional separation of bacterial cells from sample components (such as a food sample), (2) optional bacterial enrichment, (3) optional cell lysis, and/or (4) optionally nucleic acid extraction and/or purification (e.g., DNA extraction, total nucleic acid extraction (i.e., DNA and RNA), genomic DNA extraction, RNA extraction). Types of nucleic acid extracted include, but are not limited to, DNA, RNA, mRNA and miRNA.

As used herein, "presence" refers to the existence (and therefore to the detection) of a reaction, a product of a method or a process (including but not limited to, an amplification product resulting from an amplification reaction), or to the "presence" and "detection" of an organism such as a pathogenic organism or a particular strain or species of an organism.

As used herein, "detecting" or "detection" refers to the disclosure or revelation of the presence or absence in a sample of a target polynucleotide sequence or amplified target polynucleotide sequence product. The detecting can be by end point, real-time, enzymatic, and by resolving the amplification product on a gel and determining whether the expected amplification product is present, or other methods known to one of skill in the art.

The presence or absence of an amplified product can be determined or its amount measured. Detecting an amplified product can be conducted by standard methods well known in the art and used routinely. The detecting may occur, for instance, after multiple amplification cycles have been run (typically referred to an end-point analysis), or during each amplification cycle (typically referred to as real-time). Detecting an amplification product after multiple amplification cycles have been run is easily accomplished by, for instance, resolving the amplification product on a gel and determining whether the expected amplification product is present. In order to facilitate real-time detection or quantification of the amplification products, one or more of the primers and/or probes used in the amplification reaction can be labeled, and various formats are available for generating a detectable signal that indicates an amplification product is present. For example, a convenient label is typically a label that is fluorescent, which may be used in various formats including, but are not limited to, the use of donor fluorophore labels, acceptor fluorophore labels, fluorophores, quenchers, and combinations thereof. Assays using these various formats may include the use of one or more primers that are labeled (for instance, scorpions primers, amplifluor primers), one or more probes that are labeled (for instance, adjacent probes, TaqMan® probes, light-up probes, molecular beacons), or a combination thereof. The skilled person in view of the present teachings will understand that in addition to these known formats, new types of formats are routinely disclosed. The present disclosure is not limited by the type of method or the types of probes and/or primers used to detect an amplified product. Using appropriate labels (for example, different fluorophores) it is possible to combine (multiplex) the results of several different primer pairs (and, optionally, probes if they are present) in a single reaction. As an alternative to detection using a labeled primer and/or probe, an amplification product can be detected using a polynucleotide binding dye such as a fluorescent DNA binding dye. Examples include, for instance, SYBR® Green dye or SYBR® Gold dye (Molecular Probes). Upon interaction with the double-stranded amplification product, such polynucleotide binding dyes emit a fluorescence signal after excitation with light at a suitable wavelength. A polynucleotide binding dye such as a polynucleotide intercalating dye also can be used.

A "target specific polynucleotide" of the present disclosure refers to a nucleic acid sequence that is able to specifically hybridize to a gene and/or an allele and/or a portion thereof and/or a complement thereof that encodes a unique target nucleic acid sequence specific to a *Salmonella enterica* subsp. *enterica* serovar under suitable hybridization conditions and which does not hybridize with other nucleic acid sequences that do not encode for the unique target or portions thereof or complements thereof. In some embodiments, a "target-specific polynucleotide" of the disclosure is a probe or primer sequence described in SEQ ID NOS: 1-12. It is well within the ability of one skilled in the art, using the present teachings, to determine suitable hybridization conditions based on probe length, G+C content, and the degree of stringency required for a particular application.

It is expected that minor sequence variations in serovar specific target nucleotide sequences associated with nucleotide additions, deletions and mutations, whether naturally occurring or introduced in vitro, would not interfere with the usefulness of the various primer and probe nucleic acid sequences disclosed herein, as would be understood by one of skill in the art. Therefore, the scope of the present disclosure as claimed is intended to encompass minor variations in the sequences of described here and sequences having at least 90% homology to the primer and probe sequences disclosed herein.

A probe may be RNA or DNA. Depending on the detection means employed, the probe may be unlabeled, radiolabeled, chemiluminescent labeled, enzyme labeled, or labeled with a dye. The probe may be hybridized with a sample in solution or immobilized on a solid support such as nitrocellulose, a microarray or a nylon membrane, or the probe may be immobilized on a solid support, such as a silicon chip or a microarray.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, may depend upon, for example, the nature of the nucleotide sequence, temperature, and buffer conditions. These conditions may also depend on what event is desired, such as hybridization, cleavage, or strand extension. An "extracted" polynucleotide refers to a polynucleotide that has been removed from a cell. An "isolated" polynucleotide refers to a polynucleotide that has been removed from its natural environment. A "purified" polynucleotide is one that is at least about 60% free, preferably at least about 75% free, and most preferably at least about 90% free from other components with which they are naturally associated.

The words "preferred" and "preferably" refer to embodiments of the present disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the present disclosure.

The terms "comprises" and variations thereof do not have a limiting meaning where these terms appear in the description and claims. Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.). The term "and/or" means one or all of the listed elements or a combination of any two or more of the listed elements.

There are many known methods of amplifying nucleic acid sequences including e.g., PCR. See, e.g., PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. Nos. 4,683,202, 4,683,195, 4,800,159 4,965,188 and 5,333,675 each of which is incorporated herein by reference in their entireties for all purposes.

Nucleic acid amplification techniques are traditionally classified according to the temperature requirements of the amplification process. Isothermal amplifications are conducted at a constant temperature, in contrast to amplifications that require cycling between high and low temperatures. Examples of isothermal amplification techniques are: Strand Displacement Amplification (SDA; Walker et al., 1992, Proc. Natl. Acad. Sci. USA 89:392 396; Walker et al., 1992, Nuc. Acids. Res. 20:1691 1696; and EP 0 497 272, all of which are incorporated herein by reference), self-sustained sequence replication (3SR; Guatelli et al., 1990, Proc. Natl. Acad. Sci. USA 87:1874 1878), the Q.beta. replicase system (Lizardi et al., 1988, BioTechnology 6:1197 1202), and the techniques disclosed in WO 90/10064 and WO 91/03573.

Examples of techniques that require temperature cycling are: polymerase chain reaction (PCR; Saiki et al., 1985, Science 230:1350 1354), ligase chain reaction (LCR; Wu et al., 1989, Genomics 4:560 569; Barringer et al., 1990, Gene 89:117 122; Barany, 1991, Proc. Natl. Acad. Sci. USA 88:189 193), transcription-based amplification (Kwoh et al., 1989, Proc. Natl. Acad. Sci. USA 86:1173 1177) and restriction amplification (U.S. Pat. No. 5,102,784).

Other exemplary techniques include Nucleic Acid Sequence-Based Amplification ("NASBA"; see U.S. Pat. No. 5,130,238), Qβ replicase system (see Lizardi et al., BioTechnology 6:1197 (1988)), and Rolling Circle Amplification (see Lizardi et al., Nat Genet. 19:225 232 (1998)). The amplification primers of the present disclosure may be used to carry out, for example, but not limited to, PCR, SDA or tSDA. Any of the amplification techniques and methods disclosed herein can be used to practice the claimed present disclosure as would be understood by one of ordinary skill in the art.

PCR is an extremely powerful technique for amplifying specific polynucleotide sequences, including genomic DNA, single-stranded cDNA, and mRNA among others. Various methods of conducting PCR amplification and primer design and construction for PCR amplification will be known to those of skill in the art. Generally, in PCR a double-stranded DNA to be amplified is denatured by heating the sample. New DNA synthesis is then primed by hybridizing primers to the target sequence in the presence of DNA polymerase and excess dNTPs. In subsequent cycles, the primers hybridize to the newly synthesized DNA to produce discreet products with the primer sequences at either end. The products accumulate exponentially with each successive round of amplification.

The DNA polymerase used in PCR is often a thermostable polymerase. This allows the enzyme to continue functioning after repeated cycles of heating necessary to denature the double-stranded DNA. Polymerases that are useful for PCR include, for example, Taq DNA polymerase, Tth DNA polymerase, Tfl DNA polymerase, Tma DNA polymerase, Tli DNA polymerase, and Pfu DNA polymerase. There are many commercially available modified forms of these enzymes including: AmpliTaq® and AmpliTaq Gold® both available from Applied Biosystems. Many are available with or without a 3- to 5' proofreading exonuclease activity. See, for example, Vent® and Vent®. (exo-) available from New England Biolabs.

Other suitable amplification methods include the ligase chain reaction (LCR) (e.g., Wu and Wallace, Genomics 4, 560 (1989) and Landegren et al., Science 241, 1077 (1988)), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NABSA). (See, U.S. Pat. Nos. 5,409,818, 5,554517, and 6,063,603). The latter two amplification methods include isothermal reactions based on isothermal transcription, which produce both single-stranded RNA (ssRNA) and double-stranded DNA (dsDNA) as the amplification products in a ratio of about 30 or 100 to 1, respectively.

Several *Salmonella enterica* subsp. *enterica* serovars are known to cause salmonellosis in humans. Serotype definitions for *Salmonella enterica* subsp. *enterica* are known to the skilled artisan and are described for example by Grimont et al. (Grimont P. A. D., Weill F: "Antigenic formulae of *Salmonella* serovars." In., 9th edn: WHO; 2007.). Some species of *Salmonella* have the potential to be pathogenic to humans. Among these are the serovars S. Heidelberg and S. Hadar which are common contaminants of turkey meats as well as catfish, sliced deli meats, turkey burgers, eggs, and other poultry (e.g., chicks, ducklings, turkeys) and cause salmonellosis which can be marked by gastroenteritis, fever, vomiting, diarrhea, abdominal cramps, and severe dehydration and in some instances the infection can advance to sepsis and other complications including death.

Currently known methods to detect microbes of serovar S. Hadar involve using PCR and gel-based molecular serotyping techniques to detect a combination of O-antigen, phase 1 flagellar antigen and phase 2 flagellar antigen genes (Hong Y, Liu T, Lee M D, Hofacre C L, Maier M, White D G, Ayers S, Wang L, Berghaus R, Maurer J J: "Rapid screening of *Salmonella enterica* serovars Enteritidis, Hadar, Heidelberg and Typhimurium using a serologically-correlative allelotyping PCR targeting the O and H antigen alleles," *BMC Microbiol* 2008, 8:178). Antigen genes described by Hong are shown in Table 1.

TABLE 1

| Target | Type | Gene |
|---|---|---|
| O-antigen | C2 (6, 8) | abe$_2$ |
| H1 | z10 | fliC |
| H2 | e, n, x | fljB |

However, based on BLASTN searches performed herein, other *Salmonella enterica* serotypes were also found to carry each of these genes (see Table 2) and hence this method is not sufficient to differentially identify a single serotype due to cross-reactivity.

TABLE 2

| Target | Type | Gene | Other *Salmonells enterica* subsp. *enterica* matching serotypes |
|---|---|---|---|
| O-antigen | C2 (6, 8) | abe$_2$ | Newport, Muenchen |
| H1 | z10 | fliC | Haifa, Mbandaka, Lexington |
| H2 | e, n, x | fljB | Abortusequi, Chester, Mbandaka, Brandenburg, Mikawasima, Braenderup |

One assay for detection of the serovar S. Heidelberg-specific described in literature comprises molecular serotyping based on a set of four multiplex PCR reactions targeting five O-antigen loci, the fliC gene, and the fljB gene (Hong Y, Liu T, Lee M D, Hofacre C L, Maier M, White D G, Ayers S, Wang L, Berghaus R, Maurer J J: "Rapid screening of *Salmonella enterica* serovars Enteritidis, Hadar, Heidelberg and Typhimurium using a serologically-correlative allelotyping PCR targeting the O and H antigen alleles," *BMC Microbiol* 2008, 8:178). This PCR and gel-based molecular serotyping method for detection and identification of S. Hadar, S. Heidelberg, S. Enteritidis, and S. Typhimurium is based on detecting the combination of O-antigen, phase 1 flagellar antigen (H1) and phase 2 flagellar antigen genes (H2). The O: H1: H2 assignment for S. Hadar and S. Heidelberg is C2: z10: e,n,x and B: r: 1,2, respectively. However, because other *Salmonella enterica* serotypes also carry each of these genes, this method is not sufficient to differentially identify a single serotype due to cross-reactivity. In some cases a single base pair difference in the flagellin gene sequence results in an amino acid change that displays an epitope with a different serotype. Hong Y. et al. report that the H2 allelotyping primers cannot distinguish Heidelberg (B: r: 1,2) from Bradford (B: r: 1,5), Winneba (B: r: 1,6), or Remo (B: r: 1,7), or Hadar (C2: z10: e,n,x) from Glostrup (C2: z10: e,n,z15). Hence, the complexity of this assay makes it unsuitable for specific detection of S. Heidelberg or S. Hadar.

Another multiplex assay described in literature is a combination of two separate assays: the first assay detects two serovars S. Heidelberg and *S. Typhimurium* followed by a second assay that only detects *S. Typhimurium*. A positive signal from the first assay combined with the absence of a positive signal (i.e, a negative signal) from the second assay indicates the presence of S. Heidelberg (see, McCarthy N, Reen F J, Buckley J F, Frye J G, Boyd E F, Gilroy D: "Sensitive and rapid molecular detection assays for *Salmonella enterica* serovars Typhimurium and Heidelberg," *J Food Prot* 2009, 72(11):2350-2357. However, this test being a two step assay is time consuming and the potential for errors in either step leads to unreliability.

The present disclosure describes novel compositions, kits and methods for detection and in some embodiments for differential detection, of *Salmonella enterica* subsp. *enterica* serovars. Compositions, kits and methods of the present disclosure provide the ability to detect and/or distinguish between these microbial contaminants in samples including complex food samples.

In one embodiment, bioinformatic and direct DNA sequencing comparisons of several *Salmonella enterica* subsp. *enterica* serovar organisms were conducted and unique loci specific to different serovars (unique loci also described herein as "serovar specific target nucleic acids") were identified. Analysis to identify unique serovar specific target nucleic acids comprised testing an "Inclusion Panel" which comprised multiple geographically and temporally diverse strains of a first serovar of *Salmonella enterica* subsp. *enterica* and testing an "Exclusion Panel" comprising other Salmonella enterica subsp. enterica serotypes that share one or more alleles with the first serovar.

For example, for identification of unique S. Hadar serovar specific target nucleic acids, analysis comprised testing an "Inclusion Panel" which comprising multiple geographically and temporally diverse strains of S. Hadar and testing an "Exclusion Panel" comprising other *Salmonella* serotypes that share one or more alleles with S. Hadar, including the serovars Chester, Mbandaka, Brandenburg, Mikawasima, Braenderup, Newport, Haifa, Lexington, Muenchen, Istanbul, Chomedey, Abortusequi, and Glostrup.

Analysis of inclusion and exclusion panels and alignment of various known serovar sequences using custom algorithms identified several S. Hadar serovar specific target regions. Primer pairs of the disclosure were then designed to each of the serovar specific target regions to specifically amplify only the unique serovar specific target sequences against both inclusion (organism to be detected, i.e., S. Hadar) and exclusion genomes (organisms not to be detected, non-S. Hadar serovar organisms).

In another example, to identify sequences specific to S. Heidelberg, two genomes were obtained from GenBank: the complete SL476 strain (CP001120, multidrug resistant), and the draft SL486 strain (ABEL00000000, antibiotic susceptible). These genomes were run through custom algorithmsusing a set of 50 non-Heidelberg *S. enterica* genomes (complete and draft public genomes, and draft internal assemblies) as the exclusion set. This method identified 19 regions of the S. Heidelberg genome, comprising over 40 kb of sequence, that are conserved in both S. Heidelberg strains, but at least 20% divergent in all other available *Salmonella* genomes. Some of these regions were located in clusters on the chromosome. To assess specificity of these sequences beyond *S. enterica*, these candidate nucleic acid signature regions were compared by BLAST to the microbial subset of the GenBank nucleotide database. Some of the identified 19 sequences had conservation with numerous P22 phage sequences from other enteric bacteria, and were not considered any further. Regions with >80% identity to other sequences (mostly *E. coli*), were also removed from consideration and nucleic acid regions (target sequences) unique to S. Heidelberg serovar were identified. Primers and probes were then designed using the identified target sequences to achieve specific hybridization and amplification of these target sequences and/or portions thereof.

In one embodiment, unique serovar specific targets of *Salmonella enterica* subsp. *enterica* comprise: a fljB gene encoding the phase two flagellin, and/or an allele (e.g., $fljB_{e,n,x}$), a variant, a complement and/or a fragment thereof; a fliC gene encoding the phase 1 flagellin, and/or an allele (e.g., $fliC_{z10}$), a variant, a complement and/or a fragment thereof specific to S. Hadar; an arsR gene encoding a transcriptional repressor (SeHA_C3265); a phage integrase gene (SeHA_C3266); a helicase-encoding gene (SeHA_C4894, SeHA_C4896, and SeHA_C4897); a type II restriction methylase encoding gene (SeHA_C4895); or SeHA_C4893, which encodes a hypothetical protein, which are specific to S. Heidelberg. The S. Heidelberg identifiers (e.g., SeHA_CNNNN, where N=a number) are unique identifiers in the NCBI "Gene" database at http://www.ncbi.nlm.nih.gov/gene. These genes were identified on GenBank accession NC_011083.1 dated 27 Jan. 2012.

Several programs for designing primers such as Primer3 (Steve Rozen and Helen J. Skaletsky (2000) "Primer3" on the World Wide Web for general users and for biologist programmers as published in: Krawetz S, Misener S (eds) Bioinformatics Methods and Protocols: Methods in Molecular Biology. Humana Press, Totowa, N.J., pp 365-386), Primer Express® software (Applied Biosystems), and OLIGO 7 (Wojciech Rychlik (2007). "OLIGO 7 Primer Analysis Software". *Methods Mol. Biol.* 402: 35-60). In some embodiments of the present disclosure, custom primer designing software was used for primer designing and PCR primers and probes were designed for use in assays by real-time PCR to detected unambiguously, specifically and with great sensitivity *Salmonella enterica* subsp. *enterica* serovars.

In some embodiments, compositions comprising primer and/or probe sequences comprise isolated nucleic acid sequences having the nucleotide sequence of SEQ ID NOS: 1-12, complements thereof and sequences having about 90% identity to the foregoing sequences. In some embodiments, the present disclosure describes designing degenerate primers. In some embodiments the present disclosure describes designing multiplex primers that are suitable for multiplex amplification (PCR) type of assays. In some embodiments, isolated nucleic acid sequence compositions of the disclosure may further comprise one or more label, such as, but not limited to, a dye, a radioactive isotope, a chemiluminescent label, a fluorescent moiety, a bioluminescent label an enzyme, and combinations thereof.

Some embodiments describe compositions comprising a set of oligonucleotide primers for use in a multiplex amplification process (e.g. PCR) for detection of a *Salmonella enterica* subsp. *enterica* serovar, the set of oligonucleotide primers comprising: at least two primer sets, each primer set having at least a forward primer and at least a reverse primer, that are operable to specifically hybridize to a serovar specific target nucleic acids. In some embodiments, primer sets described herein are suitable for simultaneous multiplex amplification reactions.

In some embodiments, a serovar specific target nucleic acid comprises a S. Heidelberg specific gene, an allele, a variant, and/or a fragment or a complement thereof. Exemplary primer sets for amplification and/or multiplex amplification of a S. Heidelberg serovar target nucleic acid comprise one or more primer sets selected from a first primer set having SEQ ID NO: 1 and SEQ ID NO: 2; and/or a second primer set having SEQ ID NO: 4 and SEQ ID NO: 5; and/or primer sets with sequences comprising at least 90% nucleic acid sequence identity to the foregoing primers, and/or primers comprising a labeled derivative of the foregoing primer sets.

In some embodiments, a serovar specific target nucleic acid comprises a S. Hadar specific gene, an allele, a variant, and/or a fragment or a complement thereof. Exemplary primer sets for multiplex amplification of a S. Hadar serovar target nucleic acid comprise at least two primer sets selected from a first primer set having SEQ ID NO: 7 and SEQ ID NO: 8; a second primer set having SEQ ID NO: 10 and SEQ ID NO: 11; and/or primer sets with sequences comprising at least 90% nucleic acid sequence identity to any of the foregoing primer sets, and/or a primer set as described additionally comprising a labeled derivative.

The specification describes methods for detection of *Salmonella enterica* subsp. *enterica* serovar organisms from a sample and also describes methods to exclude the presence of a *Salmonella enterica* subsp. *enterica* serovar organism in a sample, wherein the detection of at least one nucleic acid sequence that is expressed in a particular serovar is indicative of the presence of a that serovar specific organism and the absence of detection of any nucleic acid sequence unique to the particular serovar is indicative of the absence of that serovar specific organism in the sample.

In one embodiment, a method of detection of a *Salmonella enterica* subsp. *enterica* serovar microorganism comprises a)

detecting the presence of a *Salmonella enterica* subsp. *enterica* serovar specific target nucleic acid sequence comprising: 1) contacting a sample with one or more probes specific to hybridize to of a *Salmonella enterica* subsp. *enterica* serovar microorganism specific target nucleic acid and 2) detecting hybridization of the one or more probe. Example probes are described in SEQ ID NO: 3, SEQ ID NO: 6, SEQ ID NO: 9 and SEQ ID NO: 12. In some embodiments, detection of specific hybridization of probes having SEQ ID NO: 3 and/or SEQ ID NO: 6 and/or a probe having 90% homology thereto and/or having a labeled derivative is indicative of the presence of a S. Heidelberg microorganism. In some embodiments, detection of specific hybridization of probes having SEQ ID NO: 9 and/or SEQ ID NO: 12 and/or a probe having 90% homology thereto and/or having a labeled derivative is indicative of the presence of a S. Hadar microorganism.

In one embodiment, a method for detection of a *Salmonella enterica* subsp. *enterica* serovar microorganism comprises: a) contacting a sample with one or more sets of oligonucleotide primers specific to hybridize to target nucleic acids specific to one or more *Salmonella enterica* subsp. *enterica* serovar specific target nucleic acid sequences; b) amplifying at least one *Salmonella enterica* subsp. *enterica* serovar specific target nucleic acid sequence by a multiplex amplification method to obtain one or more amplified *Salmonella enterica* subsp. *enterica* serovar specific nucleic acids; c) detecting the one or more amplified *Salmonella enterica* subsp. *enterica* serovar specific nucleic acids or fragments or complements thereof; and d) optionally identifying the *Salmonella enterica* subsp. *enterica* serovar specific nucleic acid; wherein detecting the one or more amplified *Salmonella enterica* subsp. *enterica* serovar specific nucleic acids or fragments or complements thereof is indicative of the presence of a *Salmonella enterica* subsp. *enterica* serovar microorganism in the sample.

In some embodiments of the present methods, one assay alone may not be definitive for detecting a *Salmonella enterica* subsp. *enterica* serovar organism due to genomic similarity between the genomic regions of other non-Salmonella or other *Salmonella* serovar organisms. Yet, when two (or more) assays such as but not limited to the assays shown in Table 3 are used either in parallel or as a multiplex assay, e.g., in a real-time TaqMan® assay, for example, where each probe in each of the two (or more) assays has a different label for distinguishing results on a real-time PCR instrument, e.g., a 7500 Fast Real-Time PCR System (Applied Biosystems), a positive result from such an assay is indicative of the presence of a particular *Salmonella enterica* subsp. *enterica* serovar organism.

In some embodiments, oligonucleotide primers that can be used in a multiplex method of the disclosure comprises two or more primer sets selected from a first primer set having SEQ ID NO: 1 and SEQ ID NO: 2; a second primer set having SEQ ID NO: 4 and SEQ ID NO: 5; a third primer set having SEQ ID NO: 7 and SEQ ID NO: 8; or a fourth primer set having SEQ ID NO: 10 and SEQ ID NO: 11 or sequences comprising at least 90% nucleic acid sequence identity thereof, or a labeled derivative thereof. In some embodiments, primers to amplify an internal positive control can also be used simultaneously in the multiplex assay. Singleplex assays comprise selecting one primer set from the primer sets described above.

In some embodiments, dual or multiplex (more than 2 assay sets) assay approach can be used to detect and distinguish between two serovars. For example, multiplexing with primers specific to both serovars followed by detection and/or identification of amplified nucleic acids indicates the presence of one or both serovars in a sample. In some embodiments, a method can comprise labeling a first primer set for detecting a first serovar specific target nucleic acid with a first label and subsequent primer sets for detecting additional serovar specific target nucleic acids with a second, a third, a fourth, etc. subsequent labels and detecting the presence of amplified fragments wherein presence of one or more serovars is identified by detecting a label of one or more amplified products. In specific embodiments, one or more S. Heidelberg and S. Hadar specific amplification products can be detected, wherein each amplification product is labeled with a different label.

Methods, in some embodiments, can include multiplex assays such as polymerase chain reactions, wherein hybridizing and amplifying of said first pair of polynucleotide primers occurs in a first vessel and said hybridizing and amplifying of said second pair of polynucleotide primers occurs in a second vessel (and hybridizing and amplifying of subsequent pairs of primers in subsequent vessels) or can comprise hybridizing and amplifying of said first pair of polynucleotide primers and said hybridizing and amplifying of said second pair of polynucleotide primers (and hybridizing and amplifying of subsequent pairs of primers) all occurs in a single vessel, the detection is a real-time assay, the real-time assay is a SYBR® Green dye assay or a TaqMan® assay.

A method of the disclosure can further comprise providing a first probe and a second probe (and additional probes such as a third probe and a fourth probe and so on), wherein the first and second probes are different from each other, the first probe operable to identify the first amplified target polynucleotide sequence and the second probe operable to identify the second amplified target nucleotide sequence, the first probe further comprises a first label and said second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye; and hybridizing the first and second probes to the PCR amplified fragments to detect the presence of the first amplified target polynucleotide sequence and the second amplified target polynucleotide sequence from the sample.

In some embodiments of a method as described above, step d) for identifying a *Salmonella enterica* subsp. *enterica* serovar specific nucleic acid comprises contacting the one or more amplified *Salmonella enterica* subsp. *enterica* serovar specific nucleic acids, fragments or complements thereof with a probe specific to hybridize to at least one of the amplified *Salmonella enterica* subsp. *enterica* serovar specific nucleic acids, fragments or complements thereof under conditions of hybridization and wherein detection of hybridization is indicative of the identity of a *Salmonella enterica* subsp. *enterica* serovar microorganism in the sample. For example, detection of hybridization with a S. Heidelberg specific probe indicates the identity of the serovar as a S. Heidelberg and detection of hybridization with a S. Hadar specific probe indicates the identity of the serovar as a S. Hadar. Exemplary probes specific to hybridize to at least one of the amplified *Salmonella enterica* subsp. *enterica* serovar specific nucleic acids, fragments or complements thereof are SEQ ID NO:3, SEQ ID NO: 6, SEQ ID NO:9 or SEQ ID NO: 12 or sequences comprising at least 90% nucleic acid sequence identity thereof, or a labeled derivative thereof.

Identification can also be done by analyzing one or more amplification products by methods such as but not limited to electrophoresis, hybridization, mass spectrometry, molecular barcoding, microfluidics, chemiluminescence, DNA sequencing and/or enzyme technologies In one example embodiment, a method of detecting a S. Heidelberg microorganism in a sample comprises: a) contacting nucleic acids present in a sample with at least one primer set, having one forward primer and one reverse primer, comprising primers selected from a first primer set having SEQ ID NO: 1 and SEQ ID NO 2 and/or a second primer set having SEQ ID NO: 4 and SEQ ID NO: 5 and/or primer sets having sequences with at least 90% homology thereto, under conditions to amplify from the sample an S. Heidelberg specific target nucleic acid or a fragment or a complement thereof; and b) detecting at least one amplified nucleic acid amplified in steps a), wherein detection of at least one amplified nucleic acid indicates the presence of a S. Heidelberg organism in the sample. In some embodiments, a multiplex amplification method using at least two primer sets selected from the primers listed above is used and detection of two amplified products is used for identification of S. Heidelberg. The multiplex method can further comprising additionally contacting nucleic acids in the sample with a primer operable to hybridize to and amplify a positive control.

In one example embodiment, a method of detecting a S. Hadar microorganism in a sample comprises: a) contacting nucleic acids present in the sample with at least one primer set, having one forward primer and one reverse primer, comprising primers selected from a first primer set having SEQ ID NO: 7 and SEQ ID NO 8 and/or sequences having at least 90% homology thereto and/or a second primer set having SEQ ID NO: 10 and SEQ ID NO: 11 and/or sequences having at least 90% homology thereto, under conditions to amplify from the sample an S. Hadar specific target nucleic acid or a fragment or a complement thereof; and b) detecting at least one amplified nucleic acid amplified in steps a), wherein detection of at least one amplified nucleic acid indicates the presence of a S. Hadar organism in the sample. In some embodiments, a multiplex amplification method using at least two primer sets selected from the primers listed above is used and detection of two amplified products is used for identification of S. Hadar. The multiplex method can further comprising additionally contacting nucleic acids in the sample with a primer operable to hybridize to and amplify a positive control.

A method of the disclosure can further comprise processing a sample. In some embodiments this can comprise steps such as but not limited to: nucleic acid extraction; and/or nucleic acid purification from microorganisms in a sample; and/or optional enrichment of microorganisms in a sample prior to nucleic acid extraction and/or purification.

In some embodiment methods, a sample to be tested for potential contamination can be tested directly or can be "prepared" or "processed" in some manner prior to molecular testing and analysis (such as by PCR). For example, a sample can be processed to separate and/or to enrich a contaminating microbe. A sample can also be further processed to separate microbial nucleic acids from the remainder of the sample by lysing microbial cells. Lysing can be accomplished using a variety of buffers that can comprise lysing agents such as but not limited to chaotropic agents, and/or enzymatic agents and/or proteases. Lysed microbial cells from a sample can be additionally processed to separate, isolate and/or extract genetic material from the microbe prior to the amplification analysis methods described herein by several methods known to the skilled artisan. For example, nucleic acid extraction can be performed by kits and reagents from Life Technologies Corporation such as The PrepSEQ™ Rapid Spin Sample Preparation Kit can be used to prepare DNA from food and/or environmental samples for use in PCR amplification reactions. Using a simple spin protocol, the PrepSEQ™ Rapid Spin efficiently prepares microbial DNA from food matrices, by forming a lysate with the DNA (but not extracting DNA), that is compatible for PCR amplification. The kit provides a fast, cost-effective solution for preparing DNA from a broad range of sample types. The PrepSEQ® Nucleic Acid Extraction Kit from Life Technologies produces high-quality bacterial DNA samples for PCR-based detection from a wide range of food and environmental samples.

Some embodiments can comprise one or more of the following steps to achieve separation of microbes and/or their nucleic acids from sample components prior to analysis of microbial nucleic acids as described herein: (1) optional bacterial enrichment to enrich certain types of bacteria (e.g., by providing conditions to selectively increase one bacterial type), (2) optional bacterial cell lysis, (3) optional nucleic acid extraction and/or purification (e.g., DNA extraction, total nucleic acid extraction (i.e., DNA and RNA), genomic DNA extraction, RNA extraction using spin columns and/or buffers and/or other known methods in the art).

In some embodiments, the disclosure describes workflows of methods for detecting and identifying one or more *Salmonella enterica* subsp. *enterica* serovar microbes: (1) prepare a PCR, or Real-time PCR reaction mix, (2) amplify the signal in a PCR instrument, (3) analyze the PCR results by visual inspection or software designed to simplify data output.

Compositions and methods of the present disclosure are ideally suited for the preparation of kits. A kit suitable for detecting the presence of a *Salmonella enterica* subsp. *enterica* serovar microorganism can comprise at least one set of oligonucleotide primers for use in an nucleic acid amplification process for the detection of a *Salmonella enterica* subsp. *enterica* serovar specific nucleic acid. Some embodiments describe a kit comprising: at least one pair of forward and reverse PCR primer sets selected from a first primer set having SEQ ID NO: 1 and SEQ ID NO 2; a second primer set having SEQ ID NO: 4 and SEQ ID NO 5; a third primer set having SEQ ID NO: 7 and SEQ ID NO: 8; and/or a fourth primer set having SEQ ID NO: 10 and SEQ ID NO 11, and/or sequences comprising at least 90% nucleic acid sequence identity thereof, or a labeled derivative thereof; and optionally at least one probe selected from probes selected from SEQ ID NO: 3, SEQ ID NO: 6, SEQ ID NO: 9 and SEQ ID NO:12 or sequences comprising at least 90% nucleic acid sequence identity thereof, or a labeled derivative thereof; and one or more components selected from a group consisting of: at least one enzyme, dNTPs, at least one buffer, at least one salt, at least one control nucleic acid sample and an instruction protocol. Some kits comprise at least two primer sets described above. Some kits comprise all the primer sets described above.

In some embodiments, kit primers can be labeled. A kit comprising multiple pairs of primers can have primer pairs each labeled with different labels that can be detected separately. Probes comprised in kits of the disclosure can be labeled. If a kit comprises multiple probes each probe can be labeled with a different label to allow detection of different amplification products that are specifically hybridized to by each different probe.

Kit components may be provided as solutions or as lyophilized powders which may be later reconstituted if needed in solutions and/or buffers which may also be provided. Components of kits may be individually and in various combinations comprised in one or a plurality of suitable container means. It is within the scope of these teachings to provide test kits for use in manual applications or test kits for use with automated sample preparation, reaction set-up, detectors or analyzers. In some embodiments, a kit amplification product may be further analyzed by methods such as but not limited to electrophoresis, hybridization, mass spectrometry, molecular barcoding, microfluidics, chemiluminescence and/or enzyme technologies.

Those having ordinary skill in the art, in light of this specification, will understand that many modifications, alternatives, and equivalents of the embodiments described above are possible. All such modifications, alternatives, and equivalents are intended to be encompassed herein.

EXAMPLES

The following procedures are representative examples of embodiments according to the disclosure that may be employed for the detection of a *Salmonella enterica* subsp. *enterica* serovar. These examples are not intended to be limiting to the scope of the claims and/or the disclosure in any way.

Example 1

Compositions & Methods to Detect *Salmonella enterica* Subsp. *Enterica* Serovar Organisms The present example describes exemplary assays designed to detect *Salmonella enterica* subsp. *enterica* serovar organisms using probe and primer sequences designed by the present inventors. Primer sequences comprising pairs of forward and reverse primers and corresponding probe sequences are shown in Table 3 below.

As shown in Table 3, an Assay ID number (such as 61163, 61172 etc.) is assigned to describe an associated primer pair (or primer pairs for multiplex assays) and associated probes that may be used for detection of a *Salmonella enterica* subsp. *enterica* serovar specific target sequence. These specific combinations of primer pairs and probe sequences have designed to selectively amplify *Salmonella enterica* subsp. *enterica* serovar specific target nucleic acid sequence regions from nucleic acids that are present in a sample suspected of being contaminated. In some embodiments these primer pairs are degenerate.

As shown in Table 3, a forward and reverse primer pair is shown in a column, which if used in an amplification reaction, will amplify the corresponding target serovar specific nucleic acid. For example, Assay ID number 61163 can be used to detect the presence of a S. Heidelberg serovar by: contacting a sample suspected of being contaminated with a forward primer, 61163F, having the nucleic acid sequence CGGTCCCTGACTAAATTCAATACCA (SEQ ID NO: 1) and a reverse primer, 61163R, having the nucleic acid sequence TCAACTGACGACATTACCTGTTCTG (SEQ ID NO: 2) under conditions to amplify a target nucleic acid sequence of an SeHA_C3265-3266 locus (or fragment or complement thereof). Melting temperatures (Tm) for forward and reverse primers are also shown in Table 3. In some embodiments, an amplified product amplified using the primers of a column can be detected using a probe described in the same column, for example in Assay ID 61163 a probe, 61163VIC, having the nucleic acid sequence ATGTGGTTCAGCTTTCTG (SEQ ID NO: 3) can be used.

Assay ID's of Table 2 can be combined to form multiplex assays. For example, one multiplex assay combines assays with Assay ID's 61163 with Assay ID 61172 and in some embodiments further with an assay to detect an internal positive control (assay not shown). Multiplex assays may be performed by simultaneously contacting a sample with the one or more primer pairs. In some embodiments, multiplex assays can be performed in parallel or can be performed sequentially.

TABLE 3

| Assay Name | Bac Track ID | Primer or Probe Names | Primer and Probe sequences 5' > 3' Sequence | probe label | Multiplex target | amp (bp) | 1X conc (nM) | Target region | Thermal Profile |
|---|---|---|---|---|---|---|---|---|---|
| *Salmonella enterica* svr. Heidelberg multiplex | 61163 | 61163F | CGGTCCCTGACTAAATTCAATACCA (SEQ ID NO: 1) | VIC/ MGB | *Salmonella* Heidelberg | 450 | | SeHA_ C3265- 3266 | FAST |
| | | 61163VIC | (VIC)ATGTGGTTCAGCTTTCTG(MGB) (SEQ ID NO: 3) | | | | 200 | | 1.95 dC, 2 min (1 rep) |
| | | 61163R | TCAACTGACGACATTACCTGTTCTG (SEQ ID NO: 2) | | | | 450 | | 2.95 dC, 30 sec |
| | 61172 | 61172F | TTGAGGCTGCATATTTGCTTTGAC (SEQ ID NO: 4) | FAM/ MGB | | | 450 | SeHA_ C4893- 4897 | 60 dC, 30 sec (40 reps) |
| | | 61172FAM | (6-FAM) TCGTTATTCCCAGGATAATG(MGB) (SEQ ID NO: 6) | | | | 200 | | |
| | | 61172R | CCGTTAAATCCGGCTTCATAGC (SEQ ID NO: 5) | | | | 450 | | |
| *Salmonella enterica* svr. Hadar multiplex | 61468 | 61468F | TGCATTAGGCAACCCGACA (SEQ ID NO: 7) | FAM/ MGB | *Salmonella* Hadar | 102 | 450 | fljB e, n, x | FAST |
| | | 61468FAM | (6-FAM))TACGGCGGCAGTCAAT (SEQ ID NO: 9) | | | | 200 | | 1.95 dC, 2 min (1 rep) |
| | | 61468R | CCCGCATCGGTATAACCACTTACA (SEQ ID NO: 8) | | | | 450 | | 2. 95 dC, 30 sec |
| | 61476 | 61476F | GGATGCCTTAAAAGCGAGTGGTAT (SEQ ID NO: 10) | VIC/ MGB | | 61 | 450 | fliC z10 | 60 dC, 30 sec (40 reps) |
| | | 61476VIC | (VIC)CTGCAACCGCATCAGCA(MGB) (SEQ ID NO: 12) | | | | 200 | | |
| | | 61476R | TTTCACTACCGTCGCAGCTT (SEQ ID NO: 11) | | | | 450 | | |

Internal Positive Control (IPC) Assays can be used with the assays described in Table 3, in parallel or in multiplex. IPC primers and probes are not described expressly herein.

Detecting can also comprise methods such as amplification, hybridization, mass spectrometry, nanostring, microfluidics, chemiluminescence, enzyme technologies and combinations thereof. Detecting steps using probes may comprise providing at least a first probe (and in some embodiments such as multiplex assays additional probes—such as a second probe, a third probe, a fourth probe etc.), wherein the first and second probes are different from each other, the first probe operable to identify the first amplified target polynucleotide sequence and the second probe operable to identify the second amplified target nucleotide sequence, the first probe further comprises a first label and said second probe further comprises a second label, wherein both labels are selected from a dye, a radioactive isotope, a chemiluminescent label, and an enzyme, the dye comprises a fluorescein dye, a rhodamine dye, or a cyanine dye, the dye is a fluorescein dye and first probe is labeled with FAM™ dye and said second probe is labeled with VIC® dye; and hybridizing the first and second probes to the PCR amplified fragments to detect the presence of the first amplified target polynucleotide sequence and the second amplified target polynucleotide sequence from the sample.

Example 2

*Salmonella* Detection in Turkey Meat Samples

The present example describes a sample preparation protocol in combination to prepare samples of turkey meat for detection of possible *Salmonella* contamination.

In some embodiment methods prior to performing a PCR assay described above in Table 3 samples can be prepared. In one example, sample preparation is by using a PrepSEQ™ Nucleic Acids Extraction Kit (Life Technologies Corporation) and a MagMAX™ Express-96 Deep Well Magnetic Particle Processor (also of Life Technology Corporation) and comprises:

Enrichment Protocol for 375 g ground Turkey meat Sample: 1. For each test portion, add 1.2 L pre-warmed (37° C.) Buffered Peptone Water (BPW) enrichment broth to 375 g of sample. 2. Mix the solution by squeezing the bag 10-15 times. Incubate at 37° C.±2° C. for 16-20 hours. 3. After incubation is complete, briefly shake the sample bags to ensure the bacteria are in solution. 4. Allow the bags to sit for 5 minutes so that the meat debris settles before removing aliquots.

Using the PrepSEQ® Nucleic Acid Extraction Kit for Food Testing (PN 4428176) and the MagMAX™ Express-96 magnetic particle processor for preparing samples.

Preparation of MagMAX Processor comprises: 1) Incubate a Magnetic Particles tube at 37° C. for 10 minutes, vortex 5 to 10 seconds, and then keep at room temperature until ready for use. White precipitate occasionally forms in the Magnetic Particles tube. Extraction experiments show that formation of precipitate does not affect performance as long as the precipitate is redissolved and the Magnetic Particles resuspended. Before using, always incubate the Magnetic Particles tube at 37° C. for 10 minutes, then vortex to completely resuspend. If after ten minutes the white precipitate is not completely dissolved, then longer incubation and higher temperatures (up to 50° C.) can be applied. 2) Prepare a Lysis Plate by carefully transferring 300 ul of pre-enriched sample to the wells. 3) Prepare the following plates: a) Elution Plate: Add 120 μl of Elution Buffer to those wells of the microtiter 96-well plate that correspond to the microtiter 96-well DW plate containing sample, as well as Lysis Buffer control. B) Wash Plates: Prepare 2 Wash Plates by aliquoting 300 μl of Wash Buffer to those wells of the microtiter 96-well plate that correspond to the microtiter 96-well DW plate containing sample, as well as Lysis Buffer control. 4) To include Elution Buffer Control, aliquot 120 μl of Elution Buffer to an extra empty well in the Elution Plate. 5) Prepare and Add the binding Premix: a) Combine 250 μL of PK Buffer with 325 μl of Binding Buffer and 25 μL of Magnetic Particles per sample; b) Vortex mixture for 5 seconds, c) Add 600 μl of binding Premix to each well d) Load the plate into the instrument when instructed by MagMax-96 on-screen menu. In some embodiments, a program such as 4428176DWPrepSEQFA program (available with the magnetic processor) is then selected on the MagMAX™ Express-96 magnetic particle processor. Press Start. Load the plates according to the readout. Verify orientation {A1 to A1}. A. Tip combs—in microtiter 96-well plate; press Start. B. Elution plate (120 uL of Elution Buffer)—In microtiter 96 well DW plate; press Start. C. Wash plate 2 (300 μL of Wash Buffer)—In microtiter 96-well DW plate; press Start. D. Wash plate 1 (300 μL of Wash Buffer—In microtiter 96-well DW plate; press Start. D. Lysis plate (sample in PK Buffer and binding PreMix)—In microtiter 96-well DW plate; press Start. When sample preparation is complete, the message "Enjoy your DNA" is displayed on the screen. Remove Elution Plate. Proceed for PCR.

PCR Procedure can be performed using a Custom TaqMan® *Salmonella* Heidelberg Assay Kit. Kit contents are set forth in the Table below:

| Kit | Component | Description |
|---|---|---|
| Custom TaqMan ® *Salmonella* Heidelberg Assay Beads | Assay beads | 1 rack of 96 lyophilized assays (12 8-tube strips) containing *Salmonella* Heidelberg specific probes and primers, internal positive control and complete reagents for Real-Time PCR |

PCR Procedure: a. Create a plate document (select Absolute Quantification (Standard Curve) from Assay drop-down list. Refer to Appendix 1 below and the appropriate instrument user guide for details. b. Create or select the following dye detectors with the Quencher Dye set to (none) or Non-Fluorescent: FAM—*Salmonella* Heidelberg target #1; VIC—*Salmonella* Heidelberg target #2; NED—Internal Positive Control. c. Associate Dyes with each reaction. d. Set thermal cycling conditions according to the following conditions: Stage 1: 95.0° C., 2:00 minutes; Stage 2: 40 repeats of [95.0° C. for 3 sec; 60.0° C. for 3 sec] e. Set Sample Volume to 30 μl. f. Select the "Fast" Run Mode for your 7500Fast instrument.

Prepare Real-Time PCR reactions as follows: a. Prepare assay beads. Remove and label an appropriate number of 8-strip tubes from the zip lock storage pouch. If needed, gently tap the tubes to move all of the assay beads to the bottom of all tubes. b. Prepare samples and controls. Thaw all reagents and place on ice. Determine the total volume of sample and controls that you need for the target assay. Each reaction requires 30 μL of sample. c. Carefully remove the caps from the 8-tube strips and discard the caps. Pipette samples or controls (30 μl) into tubes containing assay beads. Use a new pipette tip for each different sample. d. Seal each tube completely with the transparent optical strip caps provided in the kit. Strips are compatible with 7500 Fast Instrument. e. Mix by vortexing for 5 seconds at high speed. f. Spin down at 200×g for 20 seconds to collect tube contents at bottom of the tubes.

Run the reactions by: a. Open the instrument loading block and place the prepared tubes or plate in the Real-Time PCR instrument. b. Open the plate document that corresponds to the reaction plate (created in Step 1 above). c. Close the instrument loading block and start the run. Analyze the results.

Example 3

Detection of S. Hadar

Methods of the present disclosure were used to screen for S. Hadar. The present example describes an embodiment for detection from an environmental sample and comprises: 1. An environmental sample (e.g., boot swab) is placed in a stomacher bag. 2. 225 mL of modified tetrathionate media (TT) with iodine-potassium iodide (IKI) and brilliant green (BG) supplements are added to sample. 3. Sample is mixed thoroughly for a minimum of 15 seconds. 4. Sample is incubated at 35-37° C. for at least 15 h. 5. At the end of the incubation period samples are removed from the incubator. The bags are squeeze a few times to ensure sample is mixed and to let any debris settle. 6. Proceed with sample preparation as described for example in Example 1 using the PrepSEQ® Nucleic Acid Extraction Kit for Food Testing (PN 4428176) and the MagMAX™ Express-96 magnetic particle processor for preparing samples following instructions as outlined in the PrepSEQ® Nucleic Acid Extraction Kit Protocol, using the 4428176DWPrepSEQFA script. Exact enrichment time and the appropriateness of the media should be validated for each sample matrix to be tested.

PCR Procedure comprises using a Custom TaqMan® *Salmonella* Hadar Assay Kit Contents. Kit Components include: Custom TaqMan® *Salmonella* Hadar Assay, Beads, Assaybeads, 1 rack of 96 lyophilized assays (12 8-tube strips) containing *Salmonella* Hadar specific probes and primers, internal positive control and complete reagents for Real-Time PCR.

PCR Protocol: Prepare Plate document (AB instruments) a. Create a plate document (select Absolute Quantification (Standard Curve) from Assay drop-down list. Refer to Appendix 1 below and the appropriate instrument user guide for details. b. Create or select the following dye detectors with the Quencher Dye set to (none) or Non-Fluorescent: FAM—*Salmonella* Hadar target #1, VIC—*Salmonella* Hadar target #2, NED—Internal Positive Control c. Associate Dyes with each reaction. d. Set thermal cycling conditions according to the following conditions: Stage 1: 95.0° C., 2:00 minutes Stage 2: 40 repeats of [95.0° C. for 3 sec; 60.0° C. for 3 sec]. e. Set Sample Volume to 30 µl. f. Select the "Fast" Run Mode for your 7500Fast instrument. 2 Prepare Real-Time PCR reactions: a. Prepare assay beads. Remove and label an appropriate number of 8-strip tubes from the zip lock storage pouch. If needed, gently tap the tubes to move all of the assay beads to the bottom of all tubes. b. Prepare samples and controls. Thaw all reagents and place on ice. Determine the total volume of sample and controls that you need for the target assay. Each reaction requires 30 µL of sample. c. Carefully remove the caps from the 8-tube strips and discard the caps. Pipette samples or controls (30 µl) into tubes containing assay beads. Use a new pipette tip for each different sample. d. Seal each tube completely with the transparent optical strip caps provided in the kit.

Run the reactions as follows: a. Open the instrument loading block and place the prepared tubes or plate in the Real-Time PCR instrument. b. Open the plate document that corresponds to the reaction plate (created in Step 1 above). c. Close the instrument loading block and start the run.

Analyze results: a. View the amplification plots for all reactions to make sure they appear normal. b. Under Analysis Settings, for "All detectors" (FAM, VIC, and NED) select Autobaseline. c. Under Analysis Settings, for FAM and VIC detectors, select Manual Ct. For FAM and VIC detectors, Set Threshold value to 0.50. For the NED detector, set threshold value to 0.3. d. Click Analyze.

Ct cutoffs: 1. For the FAM and VIC detectors, appropriate Ct cutoff values at dRn=0.5 are applied. For initial testing, a Ct cutoff value of 35.69 for both detectors is used. 2. For the NED detector, any Ct<40 at dRn=0.3 is considered positive (+). The expected Ct range for the IPC is 30-35.

All publications and patent applications cited above are incorporated by reference in their entirety for all purposes to the same extent as if each individual publication or patent application were specifically and individually indicated to be so incorporated by reference. Although the present disclosure has been described in some detail by way of illustration and example for purposes of clarity and understanding, it will be apparent that certain changes and modifications may be practiced within the scope of the appended claims.

What is claimed is:

1. A method for detection of a *Salmonella enterica* subsp. *enterica* serovar microorganism comprising:

a) contacting a sample with one or more sets of oligonucleotide primers specific to hybridize to target nucleic acids specific to one or more *Salmonella enterica* subsp. *enterica* serovar specific target nucleic acid sequences;

b) amplifying at least one *Salmonella enterica* subsp. *enterica* serovar specific target nucleic acid sequence by a multiplex amplification method to obtain one or more amplified *Salmonella enterica* subsp. *enterica* serovar specific nucleic acids; and c) detecting the one or more amplified *Salmonella enterica* subsp. *enterica* serovar specific nucleic acids;

wherein the *Salmonella enterica* subsp. *enterica* serovar microorganism is a S. Heidelberg microorganism, and step a), b) and c) comprise:

(i) contacting nucleic acids present in the sample with at least one primer set, having one forward primer and one reverse primer, comprising primers selected from a first primer set having SEQ ID NO: 1 and SEQ ID NO 2, a second primer set having SEQ ID NO: 4 and SEQ ID NO: 5, and full complements thereof, under conditions to amplify from the sample at least one S. Heidelberg specific target nucleic acid; and (ii) detecting at least one amplified nucleic acid amplified in step (i), wherein detection of at least one amplified nucleic acid indicates the presence of a S. Heidelberg organism in the sample.

2. The method of claim 1 further comprising identifying the S. Heidelberg specific nucleic acid.

3. The method of claim 2, wherein identifying the S. Heidelberg specific nucleic acid comprises contacting the one or more amplified S. Heidelberg specific nucleic acids with a probe specific to hybridize to at least one of the amplified S. Heidelberg specific nucleic acids, fragments or complements thereof under conditions of hybridization and wherein detection of hybridization with the probe is indicative of the presence of a S. Heidelberg microorganism in the sample.

4. The method of claim 1, wherein the *Salmonella enterica* subsp. *enterica* serovar specific target nucleic acid is a fljB gene encoding a phase two flagellin, a $fljB_{e,n,x}$ gene, a fliC gene encoding a phase one flagellin, a $fliC_{z10}$ gene, an arsR gene encoding a transcriptional repressor (SeHA_C3265); a phage integrase gene (SeHA_C3266); a helicase-encoding gene (SeHA_C4894, SeHA_C4896, and SeHA_C4897); a type II restriction methylase encoding gene (SeHA_C4895); or SeHA_C4893 encoding a hypothetical protein, and alleles or variants or reverse complements of any of the foregoing genes.

5. The method of claim 3, wherein the probe specific to hybridize to at least one of the amplified S. Heidelberg specific nucleic acids comprises SEQ ID NO: 3, or SEQ ID NO: 6, or full complements thereof, or a labeled derivative thereof.

6. The method of claim 1, wherein the sample is a food sample, a beverage sample, an agricultural sample, a produce sample, an animal sample, a clinical sample, an environmental sample, a biological sample, a water sample and an air sample.

7. The method of claim 1, further comprising steps of:
nucleic acid extraction from the microorganism in the sample; and
optional enrichment of the microorganisms in the sample prior to nucleic acid extraction.

8. The method of claim 1 wherein both the first and the second primer sets are selected.

9. The method of claim 1 performed using a kit, the kit comprising:
at least one pair of forward and reverse PCR primer sets selected from a first primer set having SEQ ID NO:1 and SEQ ID NO:2, a second primer set having SEQ ID NO:4 and SEQ ID NO: 5, and full complements thereof, or a labeled derivative thereof; optionally at least one probe selected from probes selected from SEQ ID NO: 3, SEQ ID NO: 6, and full complements thereof, or a labeled derivative thereof; and
one or more components selected from a group consisting of: at least one enzyme, dNTPs, at least one buffer, at least one salt, at least one control nucleic acid sample and an instruction protocol.

10. The method of claim 1, wherein the amplifying is quantitative.

11. The method of claim 10, wherein the quantification is by a real-time polymerase chain reaction (PCR) assay.

* * * * *

SEQUENCE LISTING

```
<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggtccctga ctaaattcaa tacca                                           25

<210> SEQ ID NO 2
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 2
tcaactgacg acattacctg ttctg                                          25

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
atgtggttca gctttctg                                                  18

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttgaggctgc atatttgctt tgac                                           24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgttaaatc cggcttcata gc                                             22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tcgttattcc caggataatg                                                20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgcattaggc aacccgaca                                                 19

<210> SEQ ID NO 8
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
cccgcatcgg tataaccact taca                                              24

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tacggcggca gtcaat                                                       16

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggatgcctta aaagcgagtg gtat                                              24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tttcactacc gtcgcagctt                                                   20

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ctgcaaccgc atcagca                                                      17
```